United States Patent
Nakamura

(10) Patent No.: US 8,476,466 B2
(45) Date of Patent: Jul. 2, 2013

(54) METHOD FOR MAKING HARMFUL COMPOUND HARMLESS AND METHOD FOR PRODUCING ORGANIC SEMICONDUCTOR ELEMENT COMPOUND

(75) Inventor: Koichiro Nakamura, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 300 days.

(21) Appl. No.: 13/120,377

(22) PCT Filed: Nov. 2, 2009

(86) PCT No.: PCT/JP2009/068777
§ 371 (c)(1),
(2), (4) Date: Mar. 22, 2011

(87) PCT Pub. No.: WO2010/053072
PCT Pub. Date: May 14, 2010

(65) Prior Publication Data
US 2011/0178319 A1    Jul. 21, 2011

(30) Foreign Application Priority Data
Nov. 6, 2008   (JP) ................................ 2008-285882

(51) Int. Cl.
*C07F 9/00*     (2006.01)
*C07C 391/00*   (2006.01)

(52) U.S. Cl.
USPC .......................................... 556/70; 562/899

(58) Field of Classification Search
USPC .......................................... 556/70; 562/899
See application file for complete search history.

(56) References Cited

U.S. PATENT DOCUMENTS 8,133,912 B2 *  3/2012  Nakamura et al. ............ 514/410
2009/0326313 A1  12/2009  Nakamura et al.

FOREIGN PATENT DOCUMENTS

| EP | 2 048 148 | 4/2009 |
| JP | 2006-191947 | 7/2006 |
| JP | 2008-050265 | 3/2008 |
| WO | 2008/012948 | 1/2008 |
| WO | 2008/012953 | 1/2008 |
| WO | WO 2008/012950 A1 * | 1/2008 |

OTHER PUBLICATIONS

Nakamura, et al., "Arsenic Detoxification: Arsenic Methylation by S-containing Amino acids and Vitamin $B_{12}$ derivatives", The Chemical Society of Japan Biotechnology Symposium Koen Yoshisyu, vol. 11, Sep. 2008, p. 277, with a full English translation.

Nakamura, et al., "Photochemical Arsenic Detoxification: Effects of Photo-irradiation on Methylation of Inorganic Arsenic by Vitamin $B_{12}$ derivatives", Symposium on Photochemistry, vol. 2008, Sep. 2008, p. 57, with a full English translation.

* cited by examiner

*Primary Examiner* — Porfirio Nazario Gonzalez
(74) *Attorney, Agent, or Firm* — Hamre, Schumann, Mueller & Larson, P.C.

(57) ABSTRACT

The present invention provides a method for making a harmful arsenic compound, antimony compound and selenium compound harmless by using an organic cobalt complex, in which the cost of the method can be improved. The present invention is a method for making a harmful compound harmless, including irradiating light to an organic cobalt complex containing cobalt as a central metal and a corrin ring as a ligand, a methyl group donor, a titanium oxide photocatalyst, and a harmful compound containing an arsenic atom, an antimony atom or a selenium atom to methylate the harmful compound. In the present invention, it is preferable that the harmful compound be trimethylated.

11 Claims, 1 Drawing Sheet

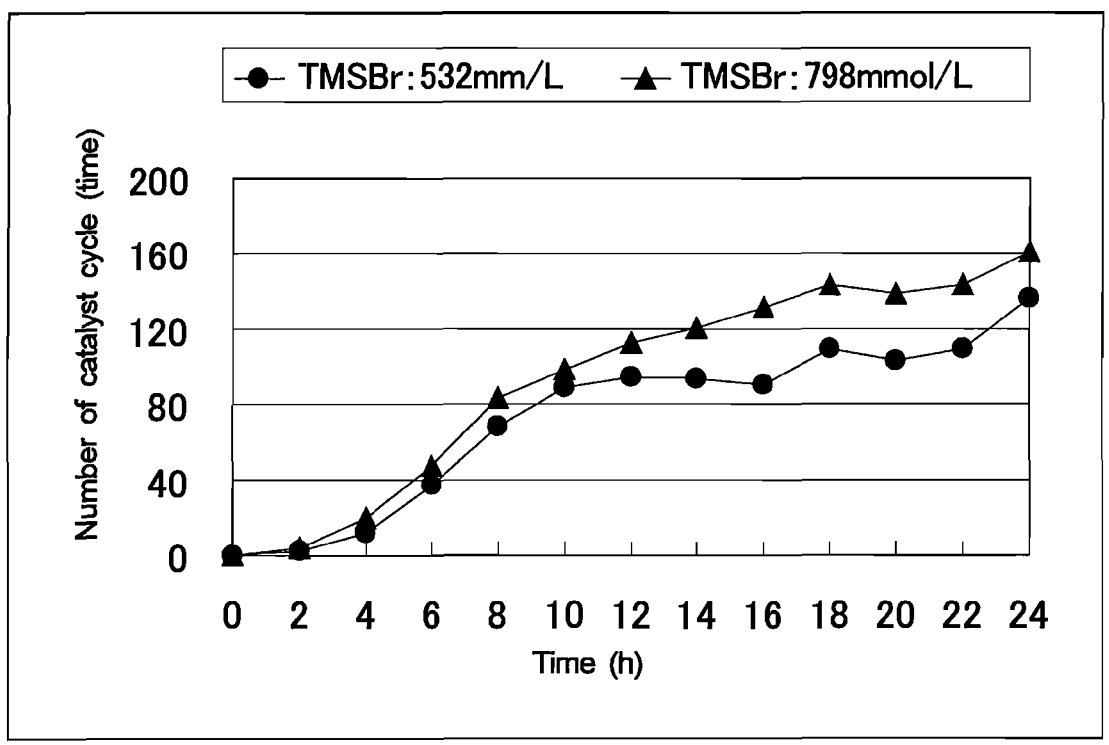

METHOD FOR MAKING HARMFUL COMPOUND HARMLESS AND METHOD FOR PRODUCING ORGANIC SEMICONDUCTOR ELEMENT COMPOUND

TECHNICAL FIELD

The present invention relates to a method for making a harmful compound containing an arsenic atom, an antimony atom or a selenium atom harmless by methylating the harmful compound. The present invention also relates to a method for producing an organic compound containing a semiconductor element (hereinafter, referred to as an organic semiconductor element compound).

BACKGROUND ART

Elements such as arsenic, antimony and selenium are widely used as industrial materials for semiconductor and the like. However, impacts of these elements on organisms are concerned when these elements leak out into the environment, since the elements can be toxic to the organisms.

Conventionally, as a method for removing these elements, a method including adding a flocculant such as poly aluminium chloride (PAC) to wastewater containing harmful inorganic arsenic such as arsenious acid to allow the arsenic to be agglutinated and adsorbed on the flocculant and iron in the raw water, and removing a precipitate by filtration after allowing the arsenic to precipitate, a method including adsorbing an arsenic compound and the like by an activated alumina or a cerium type adsorbent, and the like are commonly known.

Recently, the inventor of the present invention has proposed a method for making a harmful arsenic compound, antimony compound and selenium compound harmless by alkylating these compound using an organic cobalt complex (a vitamin $B_{12}$-type compound) (e.g., see patent literatures 1 and 2). According to these methods, the harmful arsenic compound, antimony compound and selenium compound are allowed to be harmless in an easy and simple manner with a high efficiency.

CITATION LIST

Patent Literature

[PTL 1] WO2008/012948
[PTL 2] JP-A-2008-50265

SUMMARY OF INVENTION

Technical Problem

However, with respect to the above method, there is room for improvement in cost since the organic cobalt complex (the vitamin $B_{12}$-type compound) has to be used in an amount of 3 or more equivalent with respect to a harmful arsenic compound, antimony compound and selenium compound practically when the method is performed.

Hence, a first object of the present invention is to provide a method for making a harmful arsenic compound, antimony compound and selenium compound harmless by using an organic cobalt complex, in which the cost of the method can be improved.

Further, organic compounds containing a semiconductor element (organic semiconductor element compounds), such as trimethylarsenic and t-butylarsin, are used as a material gas for semiconductor, and therefore, it is beneficial if an organic semiconductor element compound that can be used as a material gas for semiconductor can be produced from an arsenic compound, antimony compound and selenium compound, particularly from a harmful compound.

Hence, a second object of the present invention is to provide a method for producing an organic semiconductor element compound containing an arsenic atom, an antimony atom or a selenium atom from a compound containing an arsenic atom, an antimony atom or a selenium atom.

Solution to Problem

The present invention that has achieved the above first object is a method for making a harmful compound harmless, including irradiating light to an organic cobalt complex containing cobalt as a central metal and a corrin ring as a ligand, a methyl group donor, a titanium oxide photocatalyst, and a harmful compound containing an arsenic atom, an antimony atom or a selenium atom to methylate the harmful compound.

The present invention that has achieved the above second object is a method for producing an organic semiconductor element compound, including irradiating light to an organic cobalt complex containing cobalt as a central metal and a corrin ring as a ligand, an alkyl group donor, a titanium oxide photocatalyst, and a semiconductor element compound containing an arsenic atom, an antimony atom or a selenium atom.

Advantageous Effects of Invention

According to the method of the present invention for making a harmful compound harmless, the organic cobalt complex serves like a catalyst and methylation of the harmful compound occurs as a cycle reaction. Therefore, a large amount of the organic cobalt complex is not required for the methylation and thus the method is advantageous. Furthermore, since the method is carried out by light irradiation, the method is more advantageous in energy-saving comparing to the method described in the above patent literature in which a reaction is performed thermally. Consequently, a harmful arsenic compound, antimony compound and selenium compound can be made harmless with an advantage in cost.

According to the production method of the present invention, an organic semiconductor element compound that can be industrially used can be produced even from a harmful arsenic compound, antimony compound and selenium compound. It is thus beneficial.

BRIEF DESCRIPTION OF DRAWING

FIG. 1 is a graph that shows the changes of the number of catalyst cycle with the passage of time in the methylation reactions in Examples 7 and 8.

DESCRIPTION OF EMBODIMENT

First, the method of the present invention for making a harmful compound harmless will be explained.

The organic cobalt complex to be used in the method is the one containing cobalt as a central metal and a corrin ring as a ligand. The corrin ring may have a substituent. The substituent is not particularly limited as long as it does not inhibit a reaction that occurs in the method of the present invention for making a harmful compound harmless. Examples of the substituent include $CH_3$, $CH_2COZ^1$, and $CH_2CH_2COZ^2$ wherein each of $Z^1$ and $Z^2$ is $NH_2$, $OH$, $ONa$, $OCH_3$, or the like, and the substituent may be selected appropriately considering a solvent to be used in the reaction. The cobalt atom further may have a ligand besides the corrin ring as long as the ligand does not inhibit a reaction that occurs in the method of the present invention for making a harmful compound harmless. Examples of the ligand include a cyano group, a hydroxyl group, and a methyl group.

Examples of the organic cobalt complex include a vitamin $B_{12}$-type compound represented by the following formula (I), cobalamin, cobinic acid, cobinamide, cobamic acid, cobamide, and from the viewpoint of availability, the preferable one is a vitamin $B_{12}$-type compound represented by the following formula (I).

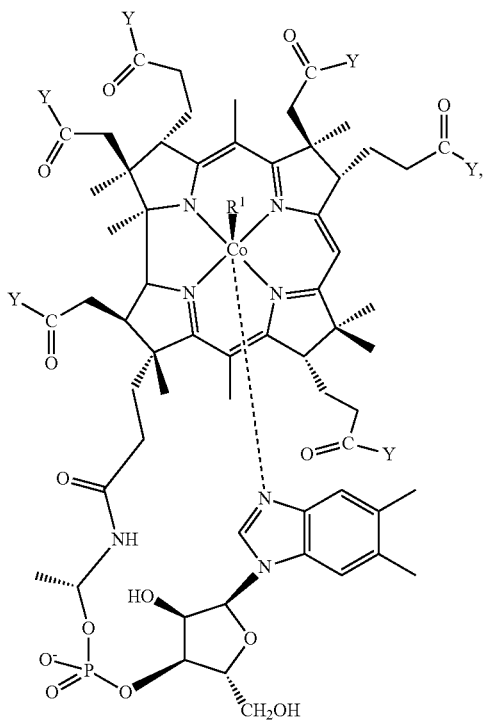

(I)

In the formula (I), $R^1$ denotes CN, OH, or $CH_3$. Each Y is the same or different and denotes $NH_2$, OH, ONa, or $OCH_3$, and from the viewpoint of availability, Y is preferably $NH_2$.

The methyl group donor is not particularly limited as long as it is a compound capable of donating a methyl group to the organic cobalt complex. Examples thereof include methyl halide, methanol, trimethylsulfoxoniuim halide, and a compound represented by $RSO_3CH_3$ wherein R denotes an alkyl group and a phenyl group optionally having a substituent. The alkyl group denoted by R is preferably an alkyl group having 1 to 6 carbon atoms. Examples thereof include a methyl group, an ethyl group, a propyl group, a n-butyl group and a t-butyl group, and particularly, a methyl group is preferable. The substituent of the phenyl group optionally having a substituent denoted by R is preferably an alkyl group having 1 to 6 carbon atoms, and particularly preferably a methyl group. The methyl group donor is preferably trimethylsulfoxoniuim halide or a compound represented by $RSO_3CH_3$ wherein R denotes a methyl group, or a phenyl group optionally having a substituent, (particularly a phenyl group and a 4-methylphenyl group).

The amount of the methyl group donor to be used is preferably 0.1 to 10000 mole with respect to 1 mole of the harmful compound, and more preferably 3 to 10000 mole because a trimethylated product of the harmful compound has fairly low toxicity.

As the titanium oxide photocatalyst, the one that is crystalline, such as titanium oxide of an anatase type, rutile type, anatase-rutile type, brookite type or the like, may be used generally.

The amount of the titanium oxide photocatalyst to be used is not particularly limited, but generally 0.01 to 70% by weight, and preferably 1 to 50% by weight with respect to the after-mentioned solvent.

The organic cobalt complex may be supported by the titanium oxide photocatalyst. In this case, it has an advantage that recovery of the organic cobalt complex and the titanium oxide photocatalyst is easy. For allowing the organic cobalt complex to be supported by the titanium oxide photocatalyst, the organic cobalt complex and the titanium oxide photocatalyst may be mixed in a solvent such as alcohol, and then they may be filtered, or the solvent is removed by evaporation.

The harmful compound means a compound that may have any negative impact on organisms when the compound leaks out into the environment and the organisms are exposed to the compound, and particularly means a compound whose 50% lethal dose ($LD_{50}$) in mice is 20 mg/kg or less.

The harmful compound containing an arsenic atom, an antimony atom or a selenium atom to be used is not particularly limited as long as it is capable of being subjected to methylation. From the viewpoint of easiness of the methylation, the harmful compound preferably includes a bond represented by M-O, M-S, M-X, M-CN, or M-Ph wherein M denotes an arsenic atom, an antimony atom or a selenium atom, X denotes a halogen atom, and Ph denotes a phenyl group. Moreover, in the preferred embodiment, the harmful compound contains an arsenic atom.

As the harmful compound containing an arsenic atom, arsenious acid, arsenic pentoxide, arsenic trichloride, arsenic pentachloride, an arsenic sulfide compound, a cyanoarsenic compound, a chloroarsenic compound, other arsenic inorganic salts, and the like are mentioned.

As the harmful compound containing an antimony atom, antimony trioxide, antimony pentoxide, antimony trichloride, antimony pentachloride, and the like are mentioned.

As the harmful compound containing a selenium atom, selenium dioxide, selenium trioxide, and the like are mentioned.

With respect to the amount of the organic cobalt complex and the harmful compound to be used, in the conventional technique, 3 mole or more of the organic cobalt complex relative to 1 mole of the harmful compound is required in order to convert the harmful compound (particularly arsenic compound) into a trimethylated compound, which has the lowest toxicity. However, in the present invention, a methylation reaction can be carried out as a cycle reaction by making use of the organic cobalt complex like a catalyst, and the amount of the organic cobalt complex to be used can be reduced even to less than 3 mole with respect to 1 mole of the harmful compound. The amount of the organic cobalt complex to be used is, for example, preferably 0.001 to 1 mole and more preferably 0.01 to 0.5 mole. In the method of the present invention for making a harmful compound harmless, it is advantageous in cost to use the organic cobalt complex in a smaller amount.

The method of the present invention for making a harmful compound harmless can be performed, for example, by mixing the organic cobalt complex, the methyl group donor, the titanium oxide photocatalyst, and the harmful compound in the presence of a solvent, and irradiating light thereto.

The light to be irradiated is not particularly limited as long as it causes the reaction. Light with a wavelength in the visible to ultraviolet region may be selected appropriately depending on the photocatalyst. From the viewpoint of the catalyst activity, ultraviolet light is preferable.

As the solvent, for example, water; water-soluble solvents such as methanol, ethanol, acetone, formaldehyde, dimethylformamide, dimethyl sulfoxide, and tetrahydrofuran; mixed solvent thereof, and the like may be used, and a water-based solvent containing methanol or formaldehyde is preferable since decomposition of an organic component in the system caused by the titanium oxide photocatalyst can be prevented.

The reaction temperature is, for example, about 10 to 300° C. and preferably a room temperature from the viewpoint of energy-saving. The reaction time is, for example, 3 min to 48 hours and preferably 5 min to 5 hours.

According to the method of the present invention for making a harmful compound harmless, methylation of the harmful compound is allowed to occur repeatedly. It is presumed that this methylation occurs according to the following mechanism. First, cobalt, which is a central metal of the organic cobalt complex, is reduced to monovalent cobalt (Co(I)) by an excited electron that is generated from an action of the titanium oxide photocatalyst by light irradiation. The Co(I) is subjected to oxidative methylation by the methyl group donor so as to be trivalent (Co(III)-$CH_3$). The Co(III)-$CH_3$ is reductively-activated by light irradiation or an excited electron of the titanium oxide photocatalyst to produce an activated methyl group. The harmful compound is methylated by this activated methyl group, and the Co(III)-$CH_3$ is demethylated so as to be reduced to divalent cobalt (Co(II)). This divalent cobalt is reduced to Co(I) again by an excited electron that is generated from an action of the titanium oxide photocatalyst by light irradiation, and then methylation of the harmful compound occurs again in the same manner as the above. As described above, methylation is performed by a cycle reaction. In this regard, when an organic cobalt complex having a methyl group such as an organic cobalt complex in which $R^1$ in formula (I) is $CH_3$ is used, a cycle reaction starts from methylation of the harmful compound.

It is preferable that the harmful compound be methylated by the method of the present invention for making a harmful compound harmless until 50% lethal dose ($LD_{50}$, in mice) of a methylated product reaches 1000 mg/kg or more.

Here, toxicity of harmful compounds containing an arsenic atom and methylated compounds of the harmful compounds are described as examples, 50% lethal dose ($LD_{50}$, in mice) of arsenious acid, which is an inorganic arsenic, is 4.5 mg/kg, and $LD_{50}$ of arsenic acid is 14 to 18 mg/kg. On the other hand, $LD_{50}$ of monomethylated arsenic (monomethylarsonic acid) is 1800 mg/kg, and $LD_{50}$ of dimethylated arsenic (dimethylarsinic acid) is 1200 mg/kg. In addition, with respect to trimethylated arsenic, $LD_{50}$ of arsenocholine is 6000 mg/kg, $LD_{50}$ of trimethylarsine oxide is 10600 mg/kg, and $LD_{50}$ of arsenobetaine is 10000 mg/kg.

As described above, from the viewpoint of the toxicity, it is preferable that the harmful compound be trimethylated particularly when the harmful compound contains arsenic. Accordingly, in the preferred embodiment of the present invention, the harmful compound is subjected to trimethylation. This trimethylation can be achieved by adjusting an amount of the methyl group donor to be added, light irradiance, and irradiation time appropriately.

Furthermore, from the viewpoint of the toxicity, it is preferable that the harmful compound be converted into a form of arsenobetaine particularly when the harmful compound contains arsenic. Accordingly, in the preferred embodiment of the present invention, the trimethylated harmful compound is reacted further with haloacetic acid.

Examples of haloacetic acid include chloroacetic acid, bromoacetic acid, and iodoacetic acid.

The reaction can be carried out by adding haloacetic acid to the reaction mixture to which light has been irradiated so that the reaction occurs.

The biggest advantage of the method of the present invention for making a harmful compound harmless is that there is no need for using a large amount of the organic cobalt complex, since the organic cobalt complex serves like a catalyst and methylation of the harmful compound occurs as a cycle reaction. Furthermore, since the method is carried out by light irradiation, the method is more advantageous in energy-saving comparing to the method described in the above patent literature in which a reaction is performed thermally. In addition, in the above-described background arts, there are some cases where a buffer solution and a reducing agent such as a substance having a SH group are added, but addition of these are not required in the present method. Consequently, the harmful compound is made harmless with an advantage in cost.

Next, the production method of the present invention will be explained.

The organic cobalt complex and the titanium oxide photocatalyst to be used for the production method of the present invention are the same as those to be used in the method of the present invention for making a harmful compound harmless.

The alkyl group donor is not particularly limited as long as it is a compound capable of donating an alkyl group to the organic cobalt complex. Examples thereof include alkyl halide, saturated aliphatic alcohols, trialkylsulfoxoniuim halide, and a compound represented by $RSO_3R'$ wherein R denotes an alkyl group, or a phenyl group optionally having a substituent, and R' denotes an alkyl group to be donated. The alkyl group that the alkyl group donor has is preferably the one having 1 to 4 carbons. Examples thereof include a methyl group, an ethyl group, a propyl group, a n-butyl group and a t-butyl group, and the alkyl group is preferably a methyl group and a t-butyl group in light of practical utility. The alkyl group denoted by R is preferably an alkyl group having 1 to 6 carbon atoms. Examples thereof include a methyl group, an ethyl group, a propyl group, a n-butyl group and a t-butyl group, and particularly, a methyl group is preferable. The substituent of the phenyl group optionally having a substituent denoted by R is preferably an alkyl group having 1 to 6 carbon atoms, and particularly preferably a methyl group. The alkyl group donor is preferably trialkylsulfoxoniuim halide or a compound represented by $RSO_3CH_3$ wherein R denotes a methyl group, or a phenyl group optionally having a substituent, (particularly a phenyl group and a 4-methylphenyl group).

The amount of the alkyl group donor to be used is preferably 0.01 to 1000 mole and more preferably 1 to 100 mole with respect to 1 mole of the semiconductor element compound.

The semiconductor element compound containing an arsenic atom, an antimony atom or a selenium atom to be used is not particularly limited as long as it is capable of being subjected to alkylation. From the viewpoint of easiness of the alkylation, the semiconductor element compound preferably includes a bond represented by M-O, M-S, M-X, M-CN, or M-Ph wherein M denotes an arsenic atom, an antimony atom or a selenium atom, X denotes a halogen atom, and Ph denotes a phenyl group. Moreover, in the preferred embodiment, the semiconductor element compound contains an arsenic atom.

As the semiconductor element compound containing an arsenic atom, arsenious acid, arsenic pentoxide, arsenic trichloride, arsenic pentachloride, an arsenic sulfide compound, a cyanoarsenic compound, a chloroarsenic compound, other arsenic inorganic salts, and the like are mentioned.

As the semiconductor element compound containing an antimony atom, antimony trioxide, antimony pentoxide, antimony trichloride, antimony pentachloride, and the like are mentioned.

As the semiconductor element compound containing a selenium atom, selenium dioxide, selenium trioxide, and the like are mentioned.

It should be noted that when the above-described harmful compound is used as a semiconductor element compound, it is of high value in the environmental aspect because the harmful compound is converted into a compound that has an industrial application.

With respect to the amount of the organic cobalt complex and the semiconductor element compound to be used, in the production method of the present invention, an alkylation reaction can be carried out as a cycle reaction by making use of the organic cobalt complex like a catalyst, and therefore, there is no need for using a large amount of the organic cobalt complex. The amount of the organic cobalt complex to be used is, for example, 0.1 to 100 mole, preferably 1 to 10 mole with respect to 1 mole of the semiconductor element compound.

The production method of the present invention can be performed, for example, by mixing the organic cobalt complex, the alkyl group donor, the titanium oxide photocatalyst, and the semiconductor element compound in the presence of a solvent, and irradiating light thereto.

The light to be irradiated is not particularly limited as long as it causes the reaction. Light with a wavelength in the visible to ultraviolet region may be selected appropriately depending on the photocatalyst. From the viewpoint of the catalyst activity, ultraviolet light is preferable. The solvent to be used is the same as that to be used for the method of the present invention for making a harmful compound harmless.

The reaction temperature is, for example, about 10 to 300° C. and preferably a room temperature from the viewpoint of energy-saving. The reaction time is, for example, 5 min to 5 hours.

In the production method of the present invention, alkylation can be carried out as a cycle reaction in the manner similar to the above-described method for making a harmful compound harmless. In the preferred embodiment of the production method of the present invention, the alkyl group donor is a methyl group donor, the semiconductor element compound contains an arsenic atom, and the semiconductor element compound is trimethylated to obtain trimethylarsenic.

As described above, according to the production method of the present invention, an organic semiconductor element compound that can be industrially used can be produced from an arsenic compound, an antimony compound and a selenium compound, particularly from a harmful compound. The production method thus is highly beneficial in the environmental aspect.

EXAMPLES

Hereinafter, the present invention will be described in more detail by way of Examples and Comparative example, but the present invention is not limited by the Examples.

Example 1

74 nmol of vitamin $B_{12}$ (cyanocobalamin) was weighed and added to an eppendorf tube A. A portion of 250 μL (325 nmol) was taken out of a 100 ppm arsenic standard solution (100 mgAs/L, 1.3 μmol/L) and added to the eppendorf tube A.

Next, a methanol solution of methyl p-toluenesulfonate (pTSM) was prepared. Specifically, 992 μL of methanol and 8 μL (52.8 μmmol, 1.69 mg in terms of sulfur) of pTSM (molecular weight: 186.23, sulfur content: 17.2 wt %, specific gravity d=1.23) were mixed in an eppendorf tube B.

250 μL of a pTSM solution was taken out of the eppendorf tube B and added to the eppendorf tube A. Thereafter, the mixture was stirred vigorously for 3 min.

50 mg of titanium oxide (Kishida Chemical Co., Ltd.) was added to a quartz cell. 500 μL of the solution in the eppendorf tube A was added to the quartz cell and the mixture was stirred vigorously. In the system, 74 nmol of vitamin $B_{12}$, 325 nmol of arsenic (inorganic trivalent arsenic) and 13.2 μmol of pTMS were contained. The quartz cell was irradiated with an ultraviolet ray for 2 hours and 4 hours using a high-pressure mercury lamp (365 nm of central wavelength, 5 mW/cm$^2$). A qualitative and quantitative analysis was performed on a yielded product using a HPLC-IPC-MS. The result of the analysis of the product is shown in Table 1.

Example 2

Example 2 was carried out in the same manner as in Example 1 except that methylcobalamin was used instead of vitamin $B_{12}$ and the ultraviolet ray was irradiated for 2 hours. The result of the analysis of the product is shown in Table 1.

Example 3

Example 3 was carried out in the same manner as in Example 1 except that hydroxocobalamin was used instead of vitamin $B_{12}$ and the ultraviolet ray was irradiated for 2 hours. The result of the analysis of the product is shown in Table 1.

Example 4

Example 4 was carried out in the same manner as in Example 1 except that methyl benzenesulfonate was used instead of pTSM and the ultraviolet ray was irradiated for 2 hours. The result of the analysis of the product is shown in Table 1.

Example 5

Example 5 was carried out in the same manner as in Example 1 except that methyl methanesulfonate was used instead of pTSM and the ultraviolet ray was irradiated for 2 hours. The result of the analysis of the product is shown in Table 1.

Example 6

Example 6 was carried out in the same manner as in Example 1 except that trimethylsulfoxoniuim bromide was used instead of pTSM and the ultraviolet ray was irradiated for 2 hours. The result of the analysis of the product is shown in Table 1.

Comparative Example 1

Comparative Example 1 was carried out in the same manner as in Example 1 except that vitamin $B_{12}$ was not used and the ultraviolet ray was irradiated for 2 hours. The result of the analysis of the product is shown in Table

TABLE 1

| | Organic cobalt complex | Methyl Group donor | Irradi- ation time (h) | Reaction product (mmol) | | | | | | | | Total of arsenic compound | Yield (%) | Methylation yield (%) | Number of catalyst cycle (Time) |
| | | | | iAs (III) | iAs (V) | MMA (III) | MMA (V) | DMA | TMAO | TeMA | UN5.91 | | | | |
|---|---|---|---|---|---|---|---|---|---|---|---|---|---|---|---|
| Ex. 1 | CC | pTSM | 0 | 0.298 | 0 | 0 | 0 | 0 | 0 | 0 | 0 | 0.298 | 92 | 0 | 0 |
| | | | 2 | 0.046 | 0.012 | 0.048 | 0.022 | 0.021 | 0.020 | 0.105 | 0.020 | 0.294 | 91 | 799 | 8.0 |
| | | | 4 | 0.041 | 0.014 | 0.043 | 0.031 | 0.019 | 0.009 | 0.119 | 0.035 | 0.311 | 96 | 827 | 8.3 |
| Ex. 2 | MC | pTSM | 2 | 0.067 | 0.027 | 0.053 | 0.027 | 0.040 | 0.027 | 0.027 | 0.000 | 0.268 | 82 | 468 | 4.7 |
| Ex. 3 | HC | pTSM | 2 | 0.067 | 0.013 | 0.053 | 0.020 | 0.020 | 0.020 | 0.013 | 0.012 | 0.218 | 67 | 306 | 3.1 |
| Ex. 4 | CC | BSM | 2 | 0.05 | 0.01 | 0.03 | 0.01 | 0.02 | 0.02 | 0.08 | 0.01 | 0.23 | 72 | 623 | 6.2 |
| Ex. 5 | CC | MSM | 2 | 0.04 | 0.00 | 0.03 | 0.00 | 0.07 | 0.06 | 0.06 | 0.00 | 0.26 | 83 | 774 | 7.7 |
| Ex. 6 | CC | TMSBr | 2 | 0.05 | 0.01 | 0.03 | 0.01 | 0.05 | 0.08 | 0.00 | 0.00 | 0.23 | 69 | 506 | 5.1 |
| C. Ex. 1 | None | pTSM | 2 | 0.200 | 0.098 | 0 | 0 | 0 | 0 | 0 | 0 | 0.298 | 92 | 0 | 0 |

CC: cyanocobalamin
MC: methylcobalamin
HC: hydroxocobalamin
BSM: methyl benzenesulfonate
MSM: methyl methanesulfonate
TMSBr: trimethylsulfoxoniuim bromide
iAs (III): inorganic trivalent arsenic
iAs (V): inorganic pentavalent arsenic
MMA (III): monomethylarsonous acid
MMA (V): monomethylarsonic acid
DMA: dimethylarsinic acid
TMAO: trimethylarsine oxide
TeMA: tetramethylarsonium ion
UN5.91: unidentified arsenic compound
Methylation yield (%) = 100 × (1 × MMA (III) + 1 × MMA (V) + 2 × DMA + 3 × TMAO + 4 × TeMA)/organic cobalt complex
Number of catalyst cycle (time) = (1 × MMA (III) + 1 × MMA (V) + 2 × DMA + 3 × TMAO + 4 × TeMA)/organic cobalt complex

Example 7

In a quartz cell, a methanol solution of methylcobalamin, arsenic (inorganic trivalent arsenic) and trimethylsulfoxoniuim bromide (TMSBr) was prepared. The total volume of the solution was 0.5 mL, the concentration of methylcobalamin was 148 μmol/L, the concentration of arsenic was 6.5 mmol/L, and the concentration of TMSBr was 532 mmol/L. Further, 50 mg of titanium oxide was mixed thereto. The quartz cell was irradiated with an ultraviolet ray for 24 hours using a high-pressure mercury lamp (365 nm of central wavelength, 5 mW/cm$^2$). A qualitative analysis was performed on a yielded product every 2 hours using a HPLC-ICP-MS, and the number of catalyst cycle was determined. The result is shown in FIG. 1.

Example 8

Example 8 was carried out in the same manner as in Example 7 except that the concentration of TMSBr was changed to 798 mmol/L. The result of the number of catalyst cycle every 2 hours is shown in FIG. 1. It should be noted that each relative ratio of products after reaction for 24 hours, which are iAs(III), iAs(V), MMA(III), DMA, TMAO, and TeMA is 1.4%, 0.5%, 2.2%, 4.3%, 91.5%, and 0%, respectively. The methylation yield on the basis of methylcobalamin was 16081%, and the number of catalyst cycle was 160 times.

As shown in Table 1, in Examples 1 to 6, the methylation yields on the basis of the catalyst (organic cobalt complex) were about 300 to 800%, and the numbers of catalyst cycle were about 3 to 8 times. Furthermore, in Examples 7 and 8 in which the concentrations of the arsenic and the methyl group donor were high, more than 100 times of the numbers of catalyst cycle could be achieved. It is thus clear that according to the present invention, an organic cobalt complex can be used like a catalyst and methylation can be efficiently performed repeatedly.

INDUSTRIAL APPLICABILITY

The method of the present invention for making a harmful compound harmless can be used to make a harmful compound containing an arsenic atom, an antimony atom or a selenium atom harmless. The production method of the present invention can be used to produce an organic semiconductor element compound, and the organic semiconductor element compound can be used as a semiconductor raw material, for example.

The invention claimed is:

1. A method for making a harmful compound harmless, comprising irradiating light to an organic cobalt complex containing cobalt as a central metal and a corrin ring as a ligand, a methyl group donor, a titanium oxide photocatalyst, and a harmful compound containing an arsenic atom, an antimony atom or a selenium atom to methylate the harmful compound.

2. The method for making a harmful compound harmless according to claim 1, wherein the organic cobalt complex is a vitamin B$_{12}$-type compound represented by a formula (I):

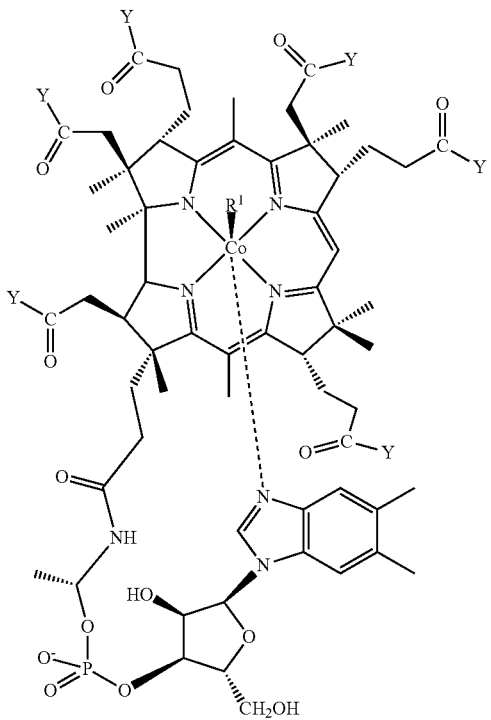
(I)

wherein $R^1$ denotes CN, OH, or $CH_3$, and each Y is the same or different and denotes $NH_2$, OH, ONa, or $OCH_3$.

3. The method for making a harmful compound harmless according to claim 1, wherein the harmful compound is trimethylated.

4. The method for making a harmful compound harmless according to claim 3, further comprising reacting the trimethylated harmful compound with haloacetic acid.

5. The method for making a harmful compound harmless according to claim 1, wherein the 50% lethal dose ($LD_{50}$, in mice) of the harmful compound is 20 mg/kg or less.

6. The method for making a harmful compound harmless according to claim 1, wherein the harmful compound includes a bond represented by M-O, M-S, M-X, M-CN, or M-Ph wherein M denotes an arsenic atom, an antimony atom or a selenium atom, X denotes a halogen atom, and Ph denotes a phenyl group.

7. The method for making a harmful compound harmless according to claim 1, wherein the harmful compound is at least one selected from the group consisting of arsenious acid, arsenic pentoxide, arsenic trichloride, arsenic pentachloride, an arsenic sulfide compound, a cyanoarsenic compound, and a chloroarsenic compound.

8. The method for making a harmful compound harmless according to claim 1, wherein the methyl group donor is methyl halide, methanol, trimethylsulfoxoniuim halide, or a compound represented by $RSO_3CH_3$ wherein R denotes an alkyl group, or a phenyl group optionally having a substituent.

9. The method for making a harmful compound harmless according to claim 8, wherein the methyl group donor is trimethylsulfoxoniuim halide or a compound represented by $RSO_3CH_3$ wherein R denotes a methyl group, or a phenyl group optionally having a substituent.

10. A method for producing an organic semiconductor element compound, comprising irradiating light to an organic cobalt complex containing cobalt as a central metal and a corrin ring as a ligand, an alkyl group donor, a titanium oxide photocatalyst, and a semiconductor element compound containing an arsenic atom, an antimony atom or a selenium atom.

11. The method for producing an organic semiconductor element compound according to claim 10, wherein the alkyl group donor is a methyl group donor, the semiconductor element compound contains an arsenic atom, and wherein the semiconductor element compound is trimethylated to obtain trimethylarsenic.

* * * * *